United States Patent [19]

Taylor et al.

[11] Patent Number: 5,100,894
[45] Date of Patent: Mar. 31, 1992

[54] OPEN CHAIN RIFAMYCIN DERIVATIVES

[75] Inventors: Peter W. Taylor, Billingshurst; Ian T. W. Matthews, Horsham; Jane I. Lowrie, London; Keith A. Menear, Horsham, all of England; Wilhelm Kump, Biel-Benken, Switzerland

[73] Assignee: Ciba-Geigy Corporation, Ardsley, N.Y.

[21] Appl. No.: 684,708

[22] Filed: Apr. 12, 1991

Related U.S. Application Data

[63] Continuation of Ser. No. 590,563, Sep. 28, 1990, abandoned, which is a continuation of Ser. No. 489,589, Mar. 7, 1990, abandoned, which is a continuation of Ser. No. 260,972, Oct. 21, 1988, abandoned.

[30] Foreign Application Priority Data

Oct. 27, 1987 [GB] United Kingdom ............... 8725118

[51] Int. Cl.$^5$ .......................................... C07D 498/12
[52] U.S. Cl. ..................................... 514/253; 514/183; 544/368; 540/459
[58] Field of Search ................. 514/253, 183; 544/368

[56] References Cited

U.S. PATENT DOCUMENTS

| 4,002,754 | 1/1977 | Cricchio et al. | 514/253 |
| 4,005,077 | 1/1977 | Bickel et al. | 540/459 |
| 4,876,258 | 10/1989 | Kump et al. | 540/458 |
| 4,916,126 | 4/1990 | Traxler et al. | 514/183 |
| 4,918,066 | 4/1990 | Kump et al. | 514/183 |
| 5,003,070 | 3/1991 | Kump et al. | 544/368 |

FOREIGN PATENT DOCUMENTS

| 239795 | 10/1986 | Fed. Rep. of Germany | 540/450 |
| 87/02361 | 4/1987 | PCT Int'l Appl. | |

OTHER PUBLICATIONS

Taguichi et al., Chem. Pharm. Bull. vol. 33, No. 5 pp. 2133-2135 (1985).

Primary Examiner—Donald G. Daus
Attorney, Agent, or Firm—JoAnn Villamizar

[57] ABSTRACT

Compounds of the general formula:

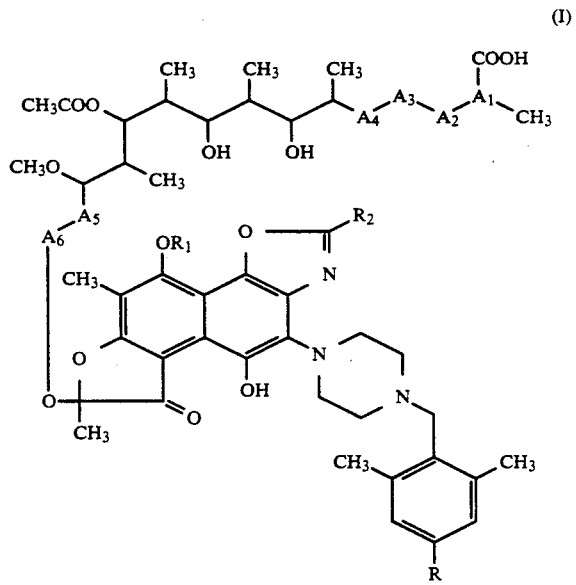

in which R is a lower alkyl group, and $R_1$ is a tri-lower alkylmethylcarbonyl group, the structure elements $-A_1-A_2-$, $A_3-A_4-$ or $A_5-A_6-$ each represent ethylene or vinylene, or the elements $-A_1-A_2-$ and $-A_3-A_4-$ each represent ethylene and $-A_5-A_6-$ represents vinylene, their optical isomers and their salts exhibit valuable pharmaceutical properties.

17 Claims, No Drawings

OPEN CHAIN RIFAMYCIN DERIVATIVES

This is a continuation of Ser. No. 590,563 filed Sept. 28, 1990, now abandoned, which is a continuation of Ser. No. 489,589 filed Mar. 7, 1990, now abandoned which is a continuation of Ser. No. 260,972 filed Oct. 21, 1988, now abandoned.

The present invention relates to new hypolipidaemic diacyl derivatives of Rifamycin.

Accordingly the present invention provides compounds of the general formula:

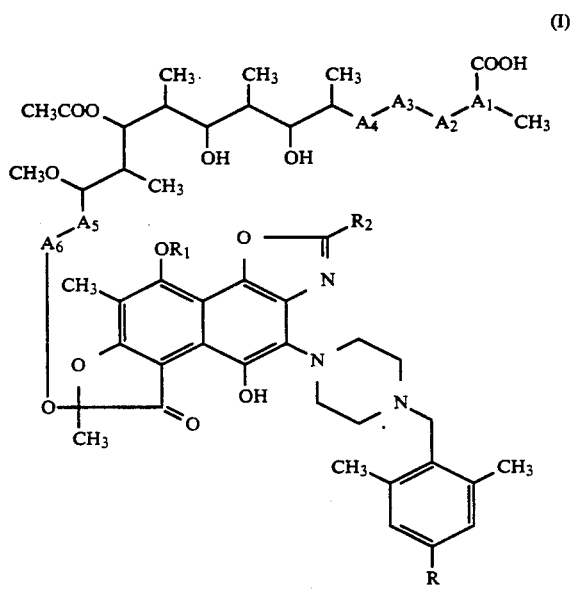

in which R is a lower alkyl group, and $R_2$ is a tri-lower alkylmethyl group $R_1$ is a tri-lower alkylmethylcarbonyl group, the structure elements $-A_1-A_2-$, $A_3-A_4-$ or $A_5-A_6-$ each represent ethylene or vinylene, or the elements $-A_1-A_2-$ and $-A_3-A_4-$ each represent ethylene and $-A_5-A_6-$ represents vinylene, their optical isomers and their salts.

The present invention also relates to the preparation of the compounds of formula (I) and to pharmaceutical compositions containing them and to their use.

The numbering employed in this specification refers to that used, for example, in U.S. Pat. No. 4,005,077.

As a lower alkyl group, R preferably contains up to 4 carbon atoms and may be ethyl, propyl, i-propyl, n-butyl, iso-butyl or tert.-butyl, but is preferably methyl.

Lower alkyl radicals in a tri-lower alkylmethylcarbonyl and tri-lower alkylmethyl radical normally contain up to and including 4, preferably up to and including 2, carbon atoms and especially one carbon atom, and are, inter alia, n-propyl, isopropyl, n-butyl or tert.-butyl, especially ethyl and more especially methyl.

Rifamycin derivatives are, for example, described in U.S. Pat. No. 4,005,077 exhibiting antituberculous activity.

In contrast, it has now been found that the novel compounds of the formula (I) surprisingly have significant hypolipidemic action. The hypolipidaemic activity of the compound of Example 1 can be tested as follows: Eight male Wistar rats, body weight 250–300 g, are divided into two groups of four. One group is dosed orally once daily at 10.00 a.m. for four days, with a solution of the compound of formula I in PEG 600 at a rate of 10 mg per kg body weight. The second group is used as a control and these are dosed at the same time with PEG 600 only. The rats are allowed free access to food. 24 hours after the last dose, the rats are anaesthetised with barbiturate and blood samples taken by cardiac puncture. 3.8% Tri-sodium citrate anticoagulant (diluted 1:7 ml blood) is added and the total cholesterol and HDL cholesterol measured using a Boehringer test kit. The test can be repeated on a second batch of eight rats, as above, except that the dose per day of compound of formula I is reduced to 1 mg/kg body weight. Thus the compounds of formula I show a significant drop in total cholesterol and in HDL cholesterol at this very low dosage.

The lipid-reducing properties can furthermore be tested in the Golden Syrian hamster which have been fed, for example, a semi-synthetic diet containing corn oil or coconut oil. Likewise, the hypolipidemic activity can be ascertained in the normolipidemic guinea pig. Furthermore, a significant reduction of plasma cholesterol levels can be determined in beagle dogs.

After treatment with compounds of the present invention the serum lipoproteins have been separated using an ultracentrifuge and have been analysed enzymatically for their content of cholesterol and triglycerides. In dose range of from approximately 1 to approximately 30 mg/kg p.o. per day, the compounds according to the invention have significantly reduced the plasma triglycide and cholesterol levels.

In classic test models for determining the antibiotic activity of rifamycin derivatives, at reasonable doses, the compounds of the compounds of the formula (I) surprisingly proved to be free from any appreciable antibiotic activity. Any antibiotic activity is regarded as disadvantageous, since it can result in the formation of strains of micro-organisms that are resistant to antibiotics, especially when the compounds are administered over a prolonged period.

Especially owing to their hypolipidemic properties the compounds according to the invention can be used as medicaments, for example, as hypolipidemics for the treatment of hyperlipidaemias, chiefly of types IIa and IIb, and for the treatment of arteriosclerosis when the presence of hyperlipoproteinaemia constitutes a risk factor.

The invention also relates to the use of the compounds according to the invention for the manufacture of medicaments, especially hypolipidaemics and antiarteriosclerotics, and for therapeutic and prophylactic treatment. The commercial formulation of the active ingredient may also be included.

The present invention especially relates to the compounds of the formula I in which the radicals $R_1$ and $R_2$ contain the same lower alkyl group.

The invention relates preferably to the compound of formula (I) where R is methyl and each $R_1$ is pivaloyl.

The invention relates especially to compounds of the formula (I) where $-A_1-A_2-$, $-A_3-A_4-$ and $-A_5-A_6-$ each represent vinylene, furthermore where $-A_1-A_2-$ and $-A_3-A_4-$ each are ethylene, and $-A_5-A_6-$ is vinylene.

The invention relates especially to the novel compounds mentioned in the Examples and to processes for their manufacture.

The invention relates also to process for the manufacture of the compounds according to the invention.

The compounds may also be in the form of their salts, particularly their pharmaceutically acceptable salts.

The compounds of formula (I) may be prepared by dissolving, in an organic solvent, a compound of the general formula (II):

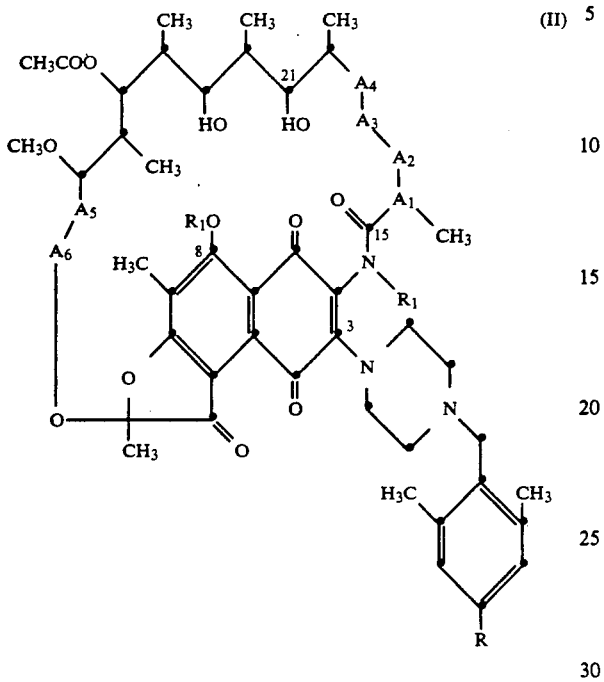

(II)

where $-A_1-A_2-$, $-A_3-A_4-$, $-A_5-A_6-$, R and $R_1$ are as defined above, heating or radiating the solution until conversion occurs and isolating the product, and if desired, separating a mixture of isomers obtainable according to the process, and/or converting a compound of the formula (I) obtainable according to the process into a different compound of the formula (I), and/or converting a salt obtainable according to the process into the free compound or into a different salt or converting a free compound obtainable according to the process into a salt.

The reactions described hereinbefore and hereinafter are carried out, if necessary, in a closed vessel, under pressure, in an inert atmosphere, for example under nitrogen and/or under unhydrous conditions.

The organic solvent may be an alcohol such as methanol, ethanol or isopropanol, a ketone, such as acetone or methyl ethyl ketone, a chlorinated hydrocarbon, such as chloroform, or trichloroethane, an ether, such as diethyl ether, a base, such as pyridine or triethylamine, or a nitrile such as acetonitrile. The preferred solvents are isopropanol and pyridine.

If the temperature is too low the conversion either does not occur or is very slow. If the temperature is too high, large amounts of unwanted by-products are formed. A suitable temperature range is from 50° to 90° C., preferably about 75° C.

The radiation is effected in a manner known per se, for example, using conventional radiation scourses, such as microwave radiation.

The resulting product may be purified by chromatography and/or by recrystallisation from a suitable solvent, such as petroleum ether.

The compounds of the formula II can be manufactured in a manner known per se, for example by treating a compound of the formula

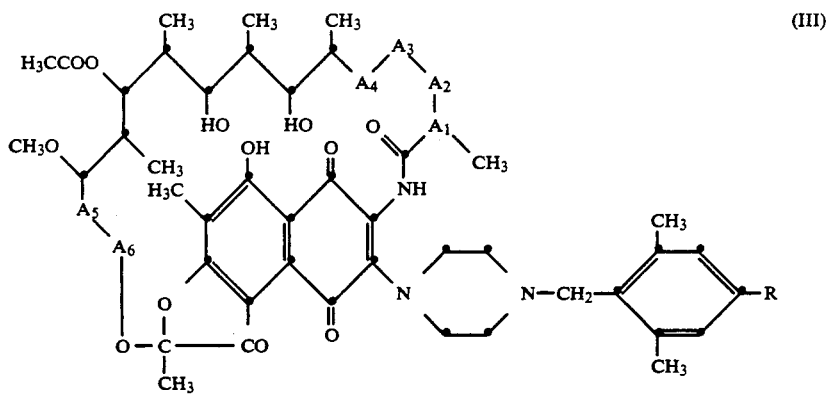

(III)

with an acylating agent that introduces a tri-lower alkylmethylcarbonyl radical into position 8, and the ring amide nitrogen atom. The compound is usually produced as mixture with an isomer having a tri-lower alkylmethylcarbonyl radical on the 8 and 21 positions. The products can be separated in known manner. The numbering used herein corresponds to the numbering used for example, in U.S. Pat. No. 4,005,077.

The introduction of the tri-lower alkylmethylcarbonyl radicals into the desired positions can be carried out in a manner known per se using a customary acylating agent suitable for the introduction of such radicals, at least two equivalents of the latter being used. It is possible to use, for example, a corresponding carboxylic acid, if necessary in the presence of a suitable condensation agent, such as dicylcohexylcarbodiimide, but preferably a reactive derivative of such a carboxylic acid, such as an anhydride, especially a mixed anhydride, such as one with an inorganic acid, such as hydrohalic acid, especially hydrochloric acid or hydrobromic acid (that is to say a corresponding acid halide, for example chloride), or with an organic acid, such as trifluoroacetic acid or a suitable mono-ester or carbonic acid, or alternatively a symmetric anhydride, or an internal anhydride, that is to say the corresponding ketene.

The derivative of a carboxylic acid employed as acylating agent is preferably used in the presence of a basic agent; a suitable basic agent is especially a non-acylatable organic base, such as a heteroaromatic base, for example pyridine, collidine or quinoline, a tertiary amine, for example triethylamine, N-ethylpiperidine, N-methylmorpholine or 1,4-dimethylpiperazine, or 1,5-diazabicyclo[5,4,0]undec-5-ene.

The acylation reactions is generally carried out in the presence of a solvent or diluent, it being possible to use as such an excess of the acylating agent or of the base, for example pyridine, used together with an acylating agent. Other solvents, which can be used, for example, also in admixture with a base, are, for example, non-acylatable organic solvents, such as hydrocarbons, for example pentane, hexane or cyclohexane, halogenated hydrocarbons, for example methylene chloride or chloroform, ethers, for example diethyl ether, ethylene glycol dimethyl ether, tetrahydrofuran or dioxan, acid esters, for example ethyl acetate, and acid amides, for example acetamide or dimethylformamide.

The reaction is generally carried out at room temperature or at slightly elevated temperatures, for example at up to approximately 70° C., the operation being carried out, if necessary, under an inert gas atmosphere. The acylation conditions, especially the amount of acylating agent used, the reaction medium, the temperature and the reaction time should be so chosen that both acyl groups are introduced, the procedure preferably being in accordance with the methods illustrated in more detail in the Examples. The course of the reaction can advantageously be followed by means of customary analytical methods especially by means of thin layer chromatography.

The working-up of the reaction product from the reaction mixture obtained according to the process is carried out in a manner known per se, for example by dilution with water and/or optionally by neutralisation or slight acidification (up to approximately pH 3) with an aqueous acid, such as an inorganic or organic acid, for example a mineral acid or, advantageously, citric acid, and by the addition of a water-immiscible solvent, such as a chlorinated hydrocarbon, for example chloroform or methylene chloride, the reaction product passing into the organic phase from which it can be obtained in purified form in customary manner, for example by drying, concentration of the solvent by evaporation and crystallization and/or chromatography of the residue, or by other customary methods or purification.

The above reaction generally yields a mixture of the two diacylated compounds, the 8-O,N-diacylated compound normally predominating. The mixture can be separated in a manner known per se, for example by means of fractional crystallisation, chromatography, etc., into the desired individual diacyl compounds.

The starting materials of the formula III are known and can be manufactured in a manner known per se;

reference is made, for example, to the PCT application having the publication No. WO 87/02361.

The conversion of compounds of formula (I) into different compounds of formula (I) can be effected in a manner known per se.

For example, compounds of formula (I), wherein $-A_1-A_2-$ and $-A_3-A_4-$ are ethylene and $-A_5-A_6-$ is ethylene or vinylene can be obtained by saturating the double bonds of the vinylene groups in a compound of formula (I), wherein $-A_1-A_2-$, $-A_3-A_4-$ and $-A_5-A_6-$ are vinylene or $-A_1-A_2-$ and $-A_3-A_4-$ are ethylene and $-A_5-A_6-$ is vinylene.

Saturation of the double bonds is carried out in a manner known per se, usually by means of catalytic hydrogenation. For this, hydrogen is used under normal or elevated pressure under heterogeneous or homogeneous catalysis conditions. Suitable catalysts for the former are metal catalysts, for example Raney metals, such as Raney nickel, or nobel metal catalysts, such as palladium, platinum, platinum oxide or rhodium which may be adsorbed on a carrier, such as calcium carbonate or barium sulphate. For homogeneous catalysis there are used, especially, complex rhodium compounds, for example tris(triphenylphosphine)rhodium(I) chloride.

The hydrogenation conditions can be modified in such a manner that the less reactive, isolated $A_5-A_6$-double bond is not simultaneously reduced, for example by discontinuing the hydrogenation when two equivalents of hydrogen have been consumed and isolating the resulting $A_1-A_2$, $A_3-A_4$- tetrahydro derivative. For this purpose, a milder catalyst is used, such as, for example, palladium on a carrier, for example activated carbon or calcium carbonate, in which case, under normal pressure and room temperature, the reaction comes to a standstill spontaneously when two equivalents of hydrogen have been consumed. When stronger catalysts are used, for example platinum, especially in the form obtainable in situ from platinum oxide by reduction, the hydrogenation may result in saturation of all three double bonds; under the conditions customarily used, the hydrogenation comes to standstill spontaneously and the corresponding hexahydro derivative is formed. The saturation of possible double bonds in starting material of the formulae II and III may be effected correspondingly.

Hydrogenation gives rise to a centre of asymmetry at carbon $A_1$ and thus to a mixture of epimers that differ from each other by the steric arrangement of the methyl group bonded to carbon atom $A_1$. Since separation of the epimers by physical methods is difficult and, in addition, involves high losses, the epimeric mixture obtained is usually isolated and used as a homogeneous process product.

The compounds of the invention include acid addition salts, especially pharmaceutically acceptable acid addition salts with inorganic or organic acids such as hydrochloric acid, hydrobromic acid, sulphuric acid, phosphoric acid, nitric or perchloric acid, aliphatic, carbocyclic, especially aromatic, or heterocyclic carboxylic or sulphonic acids, for example formic acid, acetic acid, propionic acid, succinic acid, glycolic acid, lactic acid, malic acid, tartaric acid, citric acid, fumaric acid, maleic acid, hydroxymaleic acid, pyruvic acid, phenylacetic acid, benzoic acid, p-aminobenzoic acid, anthranilic acid, p-hydroxybenzoic acid, salicyclic acid, embonic acid, methanesulphonic acid, ethanesulphonic acid, hydroxyethanesulphonic acid, ethylene disulphonic acid, halogenated benzenesulphonic acids, toluenesulphonic acid, naphthalenesulphonic acid or sulphanilic acid, methionine, tryptophan, lysine, argine or ascorbic acid.

The formation of the salts and the conversion of salts into the free compounds are carried out in a manner known per se. For example, the acid addition salts are obtained by treatment with an acid suitable for salt formation, such as one of those mentioned above, while salts can be converted into the free compounds by treatment with basic agents, such as inorganic hydroxides, carbonates and hydrogen carbonates, for organic bases and ion exchangers. These salts with the above-mentioned acids, or other salts, such as, for example, oxalates or picrates, can also be used for the purification of the resulting compounds by conveting the free compounds into salts, separating these off and recovering the free compound from the salts again. Owing to the close relationship between the compounds in free form and in the form of their salts, hereinbefore and hereinafter the free compounds should be understood as meaning also the corresponding salts, where appropriate and expedient.

Compounds of the present invention can also form internal salts, which can be obtained, for example, by customary titration to the neutral point or to the isoelectric point.

The compounds, including their salts, can also be obtained in the form of their hydrates, or their crystals can include, for example, the solvent used for crystallisation.

Depending upon the reaction and/or the type of starting materials, the compounds of the formula (I) may be obtained in the form of racemates, racemic mixtures or optical antipodes.

Resulting racemic mixtures can be separated into the pure racemates or diastereoisomers on the basis of the physico-chemical differences between the racemates in known manner, for example by chromatography and/or fractional crystallisation.

Racemates can be separated into the optical antipodes according to methods known per se, for example by recrystallisation from an optically active solvent, with the aid of suitable micro-organisms or by reaction of a compound of the formula I having salt-forming, for example basic, properties with an optically active salt-forming agent, such as an optically active acid, and separation of the mixtures of salts obtained in this manner, for example on the basis of their different solubilities, into the diastereoisomeric salts from which the antipodes can be freed, for example by treatment with a base. Resulting diastereoisomeric mixture can be separated in a manner known per se, for example by means of fractional crystallisation. Advantageously, the pharmacologically more active isomer of the more active antipode is isolated from a diastereoisomeric mixture or racemate.

The invention relates also to those embodiments of the process according to which a compound obtainable as an intermediate at any stage of the process is used as starting material and the remaining steps are carried out, or a starting material is used in form of a derivative, for example a salt, or is formed under the reaction conditions.

The starting materials used in the processes of the present invention are preferably those which result in the compounds described at the beginning as being especially valuable. The invention relates also to new starting materials which have been developed specifically for the manufacture of the compounds according to the invention, the variables having the meanings given for the compound groups of the formula (I) that are preferred in each case.

The pharmaceutical preparations according to the invention contain, for example, from approximately 10% to approximately 95%, preferably from approximately 20% to approximately 90%, of at least one active ingredient according to the invention together with at least one pharmaceutical carrier or adjunct. Pharmaceutical preparations according to the invention are, for example, those in dosage unit forms, such as dragees, tablets, capsules or suppositories, and also ampoules. Such preparations contain, per dosage unit for example, from 10 to 500 mg, preferably from 25 to 250 mg of active ingredient.

The pharmaceutical preparations of the present invention are manufactured in a manner known per se, for example by means of conventional mixing, granulating, confectioning, dissolving and lyophilising processes.

For example, pharmaceutical preparations for oral use can be obtained by combining the active ingredient with solid carriers, optionally granulating a resulting mixture and processing the mixture or granulate, if desired or necessary after the addition of suitable adjuncts, to form tablets or dragee cores. Suitable carriers are especially fillers, such as sugar, for example lactose, saccharose, mannitol or sorbitol, cellulose preparations and/or calcium phosphates, for example tricalcium phosphate or calcium bisphosphate, also binders, such as starch pastes using, for example, maize, wheat, rice or potato starch, gelatine, tragacanth, methylcellulose and/or polyvinylpyrrolidone, and or, if desired, disintegrators, such as the above-mentioned starches, also carboxymethyl starch, cross-linked polyvinylpyrrolidone, agar, alginic acid or a salt thereof, such as sodium alginate. Adjuncts are especially flow-regulating agents and lubricants, for example slica, talc, stearic acid or salts thereof, such as magnesium stearate or calcium stearate, and/or polyethylene glycol. Dragee cores are provided with suitable coatings that are optionally resistant to gastric juices, there being used, inter alia, concentrated sugar solutions which may contain gum arabic, talc, polyvinylpyrrolidone, polyethylene glycol and/or titanium dioxide, lacquer solutions in suitable organic solvents or solvent mixtures or, for the production of coatings that are resistant to gastric juices, solutions of suitable cellulose preparations, such and acetylcellulose phthalate or hydroxypropylmethylcellulose phthalate. Dyes or pigments can be added to the tablets or dragee coatings, for example for identification purposes or to indicate different doses of active ingredient.

Further pharmaceutical preparations for oral administration are dry-filled capsules consisting of gelatine and also soft, sealed capsules consisting of gelatine and a plasticiser, such as glycerine or sorbitol. The dry-filled capsules may contain the active ingredient in the form of a granulte, for example in admixture with fillers, such as lactose, binders, such as starches, and/or glidants, such as talc or magnesium stearate, and optionally stabilisers. In soft capsules, the active ingredient is preferably dissolved or suspended in suitable liquids, such as fatty oils, paraffin oil or liquid polyethylene glycols, it being possible also to add stabilisers.

As rectally administrable pharmaceutical preparations there come into consideration, for example, suppositories which consist or a combination of active ingredient with a suppository base. Suitable suppository bases are, for example, natural or synthetic triglycerides, paraffin hydrocarbons, polyethylene glycols and higher alkanols. It is also possible to use gelatine rectal capsules which contain a combination of the active ingredient with a base material; as base material there come into consideration, for example, liquid triglycerides, polyethylene glycols and paraffin hydrocarbons.

Especially suitable for parenteral administration are aqueous solutions of an active ingredient in water-soluble form, for example a water-soluble salt, also suspensions of the active ingredient, such as corresponding oily injection suspensions, therebeing used suitable lipophilic solvents or vehicles, such as fatty oils, for example sesame oil, or synthetic fatty acid esters, for example ethyl oleate or triglycerides, or aqueous injection suspensions that contain substances which increase the viscosity, for example sodium carboxymethylcellulose, sorbitol and/or dextran, and optionally, also stabilisers.

The pharmaceutical compositions of this invention can be manufactured in a manner known per se, for example by means of conventional mixing, granulating, confectioning, dissolving or lyophilising processes. For example, pharmaceutical preparations for oral use can be obtained by combining the active ingredient with solid carriers, optionally granulating a resulting mixture, and processing the mixture or granulate, if desired or necessary after the addition of suitable adjuncts, to form tablets or dragée cores.

The invention relates also to the use of the compounds of the general formula I and their pharmaceutically acceptable acid addition salts as medicaments, especially as hypolipidaemics, preferably in the form of pharmaceutical preparations. The dosage depends upon the species of warm-blooded animal, the age and individual condition of the warm-blooded animal to be treated and upon the method of administration. The daily doses administered are between approximately 1 and approximately 100 mg/kg and preferably, for example for warm-blooded animals of approximately 70 kg body weight, between approximately 3 and approximately 50 mg/kg.

The invention is illustrated by the following Examples, but the scope is not limited in any way.

EXAMPLE 1

A solution of 8-O,N-dipivaloyl-3-[4-(2,4,6-trimethylbenzyl)piperazin-1-yl]-rifamycin S (0.75 g, 0.69 mmol) in dry pyridine (35 ml) is heated at 75° C., under an atmosphere of nitrogen. After 6 hours the deep purple solution changes to a deep red colour. Thin layer chromatography (silica, 2% methanol in chloroform) shows the reaction product as a red spot with an Rf at 0.15.

The solvent is then removed under reduced pressure and the resulting crude product purified by flash chromatography (2% methanol in chloroform, silica, Rf 0.15) to give the compound of formula (I) in which R is methyl, $R_1$ is pivaloyl and $R_2$ is t-butyl and the structure elements -$A_1$-$A_2$-, -$A_3$-$A_4$- and -$A_5$-$A_6$- each represent vinylene as a deep red solid. Recrystallisation from petroleum ether gives the pure product having a melting point 113°–115° C. dec. It has the following elemental analysis:

Expected: C 67.69%; H 7.73%; N 3.88%
Found: C 67.84%; H 7.88%; N 3.88%

The mass spectrum gives M⊕ at 1082, in agreement with the proposed structure.

| $^1$H NMR (300 MHz in CDCl$_3$): | |
|---|---|
| 7.23 | (1H, dd, J=11.3, 16.2Hz, H-18) |
| 6.88 | (2H, s, aromatic protons) |
| 6.55 | (1H, d, J=11.4Hz, H-17) |
| 6.11 | (1H, dd, J=6.6, 16.8Hz, H-19) |
| 5.25 | (1H, .brs, H-28) |
| 5.13 | (1H, brd, J=7.2Hz, H-25) |
| 4.08 | (1H, brs, —OH) |
| 3.59–3.79 | (6H, M, piperazine CH$_2$, H-21 and N—CH$_2$—Ar) |
| 3.35 | (1H, brs, H-27) |
| 3.05 | (1H, M, H-23) |
| 3.02 | (3H, s, —OCH$_3$) |
| 2.68 | (4H, brs, piperazine CH$_2$) |
| 2.41 | (6H, s, ArCH$_3$ (ortho)) |
| 2.26 | (3H, s, ArCH$_3$ (para)) |
| 2.19 | (3H, s, H-14) |
| 2.08 | (3H, s, H-36) |
| 1.95 | (3H, s, H-30) |
| 1.78 | (3H, s, H-13) |
| 1.56 | (9H, s, t-butyl) |
| 1.46 | (9H, s, pivaloyl CH$_3$) |
| 1.06 | (3H, d, J=6.6Hz, ansa chain CH$_3$) |
| 0.96 | (3H, d, 6.6Hz, ansa chain CH$_3$) |
| 0.73–0.93 | (3H, M, ansa CH$_3$) |
| 0.71 | (3H, d, J=6.6Hz, ansa CH$_3$) |
| $^{15}$N N.M.R. | (CDCl$_3$, Reference liquid NH$_3$, nitromethane standard) 238.50, 60.50 and 47.40. |

The starting material can be obtained as follows:

a) A solution of 50 g rifamycin S in 500 ml dioxan, is treated with 30 g N-(2,4,6-trimethylbenzyl)-piperazine and allowed to stand for 18 hours at room temperature. Then it is acidified by adding 10% aqueous citric acid solution, and the reaction product is taken up in methylene chloride. After drying and evaporation of the methylene chloride extract, the dark-coloured residue is dissolved in ethanol and treated, dropwise, with aqueous ascorbic acid. The 3-[4-(2,4,6-trimethylbenzyl)-piperazin-1-yl]-rifamycin SV precipitates in the form of yellow crystals of m.pt. 178°–81° C. (partial decompsn).

Analogous result is obtained by reacting 20 g 3-bromorifamycin S with 20 g N-(2,4,6-trimethylbenzyl)-piperazine in 200 ml tetra-hydrofuran over 30 minutes at room temperature and then working-up as above.

b) A solution of 10 g of the product produced according to a) of the SV series in 200 ml of methylene chloride is vigorously stirred for 5 minutes with 10 g of finely-powdered MnO$_2$. The solid component is filtered off and the filtrate evaporated to dryness, whereby blue-black amorphous 3-[4-(2,4,6-trimethylbenzyl)-piperazin-1-yl]-rifamycin S results which is sufficiently pure for the acylation.

c) To a solution of 25 g 3-[4-(2,4,6-trimethylbenzyl)-piperazin-1-yl]-rifamycin S in 250 ml pyridine is added dropwise 35.5 ml pivaloyl chloride (10.5 equivs) and the mixture stirred at room temperature for 8 hours, until all starting material disappears in the thin-layer chromatogram. 150 ml methanol, are then added to the solution and the whole is stirred at room temperature for 1 hour, to decompose excess pivaloyl chloride, and evaporated to dryness. The residue is taken up in 300 ml methylene chloride, the solution filtered and the filtrate extracted with 300 ml water. The aqueous phase is adjusted to pH 2 with 1N HCl and extracted three times with methylene chloride. The combined methylene chloride extracts are washed three times with 100 ml water each time, dried and evaporated to dryness. The residue (29 g) is applied to a column of 1 kg silica gel and eluted with a mixture of ethyl acetatecyclohexane (1:4). The early fractions contain 8-O, 21-O-dipivaloyl-3-[4-(2,4,6- trimethylbenzyl)-piperazinyl]-rifamycin S, which is obtained, by further chromatography on silica gel and crystallisation from ether, as violet-brown crystals of m.pt. 135°–145° C. (decompsn). The subsequent fractions contain the main product i.e. 8-O, N-dipivaloyl-3-[4-(2,4,6-trimethylbenzyl)-piperazin-1-yl]-rifamycin S which forms, crystallised from diethyl ether, red-violet crystals of m.pt. 157°–163° C.

EXAMPLE 2

A solution of 8-O, N-dipivaloyl-3-[4-(2,4,6-trimethylbenzyl)-piperazin-1-yl]-rifamycin S (100 mg, 92 μmol) in iso-propanol (3 cm$^3$) under an atmosphere of dry nitrogen is heated under reflux for 5 hours. The reaction is followed to a maximum by t.l.c. (silica, 3% CH$_3$OH/CHCl$_3$) after which time the reaction mixture is cooled and the solvents removed under reduced pressure. The crude reaction product is then purified by flash chromatography (3% CH$_3$OH/CHCl$_3$, Rf 0.15, silica) to afford the reaction product, as a deep red solid. Recrystallisation from petroleum ether gave the same product as in Example 1 as deep red amorphous crystals (m.p. 113°–115° C.) and having the same characterising data as the product of Example 1. A second product was isolated (Rf. 0.433) also as a deep red solid and corresponds to a mono-pivaloylated substrate.

EXAMPLE 3

8-O, N-dipivaloyl-3-[4-(2,4,6-trimethylbenzyl)-piperazin-1-yl]-rifamycin S (54.5 mg, 0.0505 mmoles) is dissolved in acetonitrile (200 μl) and subjected to microwave radiation (full power, 600 W) for 20 minutes. t.l.c. (CHCl$_3$/CH$_3$OH 97%) showed considerable conversion to the same product as in Example 1. Purification is achieved by silica gel chromatography (28×1 ml CHCl$_3$/CH$_3$OH 97%). The product, homogeneous on the t.l.c. and having the same characterising data as the product of Example 1 is obtained.

EXAMPLES 4–10

In a manner analogous to that described in Example 1, the following compounds can be made with R, R$_1$ and R$_2$ in the compound of formula (I) being as shown in the Table.

| Example | R | R$_1$ | R$_2$— |
|---|---|---|---|
| 4 | tert-butyl | pivaloyl | t-butyl |
| 5 | methyl | 2,2-dimethyl-butyryl | 1,1-dimethylpropyl |
| 6 | methyl | 2-ethyl-2-methylbutyryl | 1-ethyl-1-methyl-propyl |
| 7 | methyl | 2,2-diethyl-butyryl | 1,1-diethylpropyl |
| 8 | methyl | 2,2-dimethyl-valeryl | 1,1-dimethylbutyl |
| 9 | methyl | 2-ethyl-2-methylvaleryl | 1-ethyl-1-methyl-butyl |
| 10 | tert-butyl | 2,2-diethyl-butyryl | 1,1-diethylpropyl |

EXAMPLE 11

A solution of 2.0 g of the derivative obtained in example 1 in 50 ml ethanol is hydrogenated at 22° C. and normal pressure in the presence of 0.2 g Pd-catalyst (10% Pd on carbon). After 16 hours and a H$_2$-uptake of 76 ml the catalyst is removed from the reaction mixture by filtration over celite and the filtrate is evaporated to dryness. The remaining material is purified by twofold column-chromatography on silica gel, using methylene chloride/methanol 20:1 as an eluant. After removing a small amount of red material in a weak, faster moving band the main product is eluted in pure form in a strong, dark-red band, as the tetrahydro-derivative (-A$_1$-A$_2$- and -A$_3$-A$_4$- each represent ethylene) of the compound obtained according to Example 1.

Mass-spectra (FAB+,-): M=1085 (C$_{61}$H$_{87}$N$_3$O$_{14}$)

$^1$H-NMR-spectrum (360 MHz, MeOD, ppm from TMS): only 2 remaining olefinic protons (H-28, 29) at 6.27 (d, 1H) and ~5.3 (in m together with H-25). CH$_3$-30 in m at ~0.7.

UV-spectrum (EtOH, λ$_{max}$/ε$_{max}$): 261/35680, 327/13320, 415/5760, 498/6600.

EXAMPLE 12

Capsules containing 0.25 g of the active substance, for example, the compound characterised in Example 1, are produced as follows:

Composition (for 1000 capsules):

| active substance | 250.0 g |
|---|---|
| corn starch | 50.0 g |
| polyvinylpyrrolidone | 15.0 g |
| magnesium stearate | 5.0 g |
| ethanol | q.s. |

The active substance and the corn starch are mixed together and moistened with a solution of the polyvinylpyrrolidone in 50 g of ethanol. The moist mass is forced through a sieve having a mesh width of 3 mm and dried at 45° C. The dry granulate is passed through a sieve having a mesh width of 1 mm and mixed with 5 g of magnesium stearate. The mixture is introduced in 0.320 g portions into size O dry-filled capsules.

EXAMPLE 13

Tablets containing 250 mg of the active substance, for example, the compound characterised in Example 1, are produced as follows:

Composition (for 1 tablet):

| active substance | 250 mg |
|---|---|
| microcrystalline cellulose | 80 mg |
| sodium carboxymethyl starch | 10 mg |
| magnesium stearate | 3 mg |
| talc | 7 mg |
| | 350 mg |

The active substance is mixed homogeneously with the additives and pressed to form tablets.

For the manufacture of film-coated dragees, the tablets are each coated with 1 mg of aqueous lacquer.

Instead of sodium carboxymethyl starch, it is possible to use sodium carboxymethylcellulose.

EXAMPLE 14

Dry-filled containing 100 mg of the active substance, for example, the compound characterised in Example 1, are manufactured as follows:

Composition (for 1000 capsules):

| active substance | 100.00 g |
|---|---|
| lactose | 50.00 g |
| ethylcellulose | 1.50 g |
| stearic acid | 1.50 g |

-continued

| | |
|---|---|
| | 153.00 g |

The active substance is mixed with the lactose and the resulting mixture is moistened with a solution of ethylcellulose in 10 times its amount by weight of methylene chloride, beaten through a sieve having a mesh width of 3-5 mm and dried at a temperature not exceeding 40° C. The dry granulate is beaten through a sieve having a mesh width of 0.5 mm and mixed with the pulverulent stearic acid. The mixture is then introduced in 0.153 g portions into size 2 dry-filled capsules.

EXAMPLE 15

Dry ampoules of phials containing 500 mg of the active substance, for example, the compound characterised in Example 1, can be produced as follows:

Composition (for 1 ampoule of phial):

| | |
|---|---|
| active substance | 0.5 g |
| mannitol | 0.05 g |
| water | |

Under aseptic conditions, a sterile aqueous solution of the active substance and the mannitol are sealed in 5 ml ampoules or 5 ml phials and tested.

We claim:

1. A compound of the formula (I)

[chemical structure]

in which R is a lower alkyl group, $R_1$ is a tri-lower alkylmethylcarbonyl group, and $R_2$ is a tri-lower alkylmethyl group, the structure elements $-A_1-A_2-$, $A_3-A_4-$ or $A_5-A_6-$ each represent ethylene or vinylene, or the elements $-A_1-A_2-$ and $-A_3-A_4-$ each represent ethylene and $-A_5-A_6-$ represents vinylene, their optical isomers and their salts.

2. A compound according to claim 1 in which $-A_1-A_2-$, $-A_3-A_4-$ and $-A_5-A_6-$ each represent vinylene, and salts thereof.

3. A compound according to claim 1 in which $-A_1-A_2-$ and $-A_3-A_4-$ each are ethylene, and $-A_5-A_6-$ is vinylene, and salts thereof.

4. A compound according to claim 1 in which R is methyl, and salts thereof.

5. A compound according to claim 1 in which $R_1$ and $R_2$ contain the same lower alkyl group, and salts thereof.

6. A compound according to claim 1 in which R, and $R_2$ have up to and including 4, preferably 2, carbon atoms in each lower alkyl group, and salts thereof.

7. A compound according to claim 1 in which $R_1$ is pivaloyl.

8. A compound according to claim 1 in which R is methyl and $R_1$ is pivaloyl, and $R_2$ is t-butyl and salts thereof.

9. A pharmaceutical composition containing a antihyperlipidaemically and/or antiarlenoseleroically effective amount of a compound as claimed in claim 1 or a pharmaceutically acceptable salt thereof and a pharmaceutically acceptable excipient or carrier.

10. A method for the treatment of hyperlipidaemias and arteriosclerosis in a patient in need thereof comprising administering to said patient a pharmaceutically acceptable amount of a compound of the formula (I)

[chemical structure]

in which R is a lower alkyl group, $R_1$ is a tri-lower alkylmethylcarbonyl group and $R_2$ is a tri-lower alkylmethyl group, the structure elements $-A_1-A_2-$, $A_3-A_4-$ or $A_5-A_6-$ each represent ethylene or vinylene, or the elements $-A_1-A_2-$ and $-A_3-A_4$ each represent ethylene and $-A_5-A_6-$represents vinylene, optical isomers thereof or a pharmaceutically acceptable salt thereof.

11. A method according to claim 10 wherein $-A_1-A_2-$, $-A_3-A_4-$ and $-A_5-A_6-$ each represent vinylene, and pharmaceutically acceptable salts thereof.

12. A method according to claim 10 in which $-A_1-A_2-$and $-A_3-A_4-$ each are ethylene, and $-A_5-A_6-$ is vinylene, and salts thereof.

13. A method according to claim 10 in which R is methyl, and pharmaceutically acceptable salts thereof.

14. A method according to claim 10 in which $R_1$ and $R_2$ contain the same lower alkyl groups and pharmaceutically acceptable salts thereof.

15. A method according to claim 10 in which $R_1$ and $R_2$ have up to and including 4, preferably 2, carbon atoms in each lower alkyl group, and pharmaceutically acceptable salts thereof.

16. A method according to claim 10 in which $R_1$ is pivaloyl.

17. A method according to claim 10 in which R is methyl and $R_2$ is t-butyl and pharmaceutically acceptable salts thereof.

* * * * *